(12) United States Patent
Rawicz et al.

(10) Patent No.: US 6,244,863 B1
(45) Date of Patent: Jun. 12, 2001

(54) DENTAL COLOR COMPARATOR SCOPE

(76) Inventors: Andrew H. Rawicz, 7216 Hewitt Str., Burnaby BC (CA), V5A 3M2; Pawel Kowalski, 459 Ailsa Ave., Port Moody BC (CA), V3H 1A2; Ivan Melnyk, 604 Cottonwood Ave., Coquitlam BC (CA), V3J 2S4

( * ) Notice: Subject to any disclaimer, the term of this patent is extended or adjusted under 35 U.S.C. 154(b) by 0 days.

(21) Appl. No.: 09/523,527

(22) Filed: Mar. 10, 2000

(51) Int. Cl.⁷ ................................................. A61C 19/10
(52) U.S. Cl. .......................... 433/26; 356/424; 356/421; 433/29
(58) Field of Search .................. 433/29, 26; 356/408, 356/421, 422, 423, 424

(56) References Cited

U.S. PATENT DOCUMENTS

| | | | |
|---|---|---|---|
| 1,469,893 | * 10/1923 | Claff | 433/26 |
| 2,502,014 | * 3/1950 | Loggie | 356/421 |
| 3,436,156 | * 4/1969 | Adler et al. | 356/423 |
| 3,436,157 | * 4/1969 | Adler et al. | 433/26 |
| 4,654,794 | * 3/1987 | O'Brien | 433/26 |
| 4,836,674 | * 6/1989 | Lequime et al. | 433/26 |
| 5,055,040 | * 10/1991 | Clar | 433/29 |
| 5,690,486 | * 11/1997 | Zigelbaum | 433/29 |
| 5,871,351 | * 2/1999 | Jung et al. | 433/29 |
| 5,967,775 | * 10/1999 | Shahid et al. | 433/29 |

* cited by examiner

Primary Examiner—Todd E. Manahan (57) ABSTRACT

A dental comparator scope for comparing a dental shade to a natural tooth. The scope comprises an L-shape body which includes a sight applying to the tooth and a handle for holding the scope, and a cartridge with a plurality of dental shades in it. Two identical optical channels are mounted, one inside of the sight and another inside of the handle. The channels include lenses and polychromatic light sources, preferable white LEDs. A mirror is placed in a point where optical axes of the channels are crossing. A split image of the shade and the tooth is observed through an eyepiece. The shades in the cartridge are driven by a motor when a button on the body is pressed by finger. The motor, light sources and adjuvant electronics are powered by a battery which is placed in the handle. The cartridge is snapped to the handle in a steady position. According to yet another embodiment, the cartridge can be shifted toward and backward the tooth and different zones of the shade can be compared with the correspondent zones of the tooth.

24 Claims, 13 Drawing Sheets

DENTAL COLOR COMPARATOR SCOPE

BACKGROUND OF THE INVENTION

1. Field of the Invention

The invention in general relates to dental devices. More particularly, this invention relates to a device for accurate selection of standard colored dental shades to natural teeth.

2. State of the Art

The accuracy of color matching of dental prostheses (or prosthetic teeth) to natural teeth is very often considered as a crucial factor determining the quality of dental restorative work. For this reason, a dentist must make a decision as to the color to be used for dental prostheses such that the dental prostheses appear natural when implanted adjacent to natural teeth. The dentist generally refers to standard colored dental shades which he or she chooses by putting the shades against the natural teeth. The shades are typically preformed plastic or ceramic dental prostheses with certain varieties of hue, color and saturation. By holding the shade with a thin metallic holder and positioning the shade close to an adjacent referenced natural tooth the dentist decides which shade is the closest in color to the tooth. The decision is formulated in prescription to the dental lab that makes plastic, ceramic or composite dental prostheses of certain color based on standardized recipes.

The procedure of visually choosing the best matching shade often appears to be difficult. First, the color appearance depends on illumination conditions, namely light intensity and its spectral composition, or in another words, color. This problem is a common one in colorimetry that arises from the different sensitivity of the human eye (photopic and scotopic observer). In the case of natural teeth, this problem is magnified by the translucency of the teeth because illuminated light is absorbed by enamel and dentin, and then, it is scattered back. A background against which natural teeth and shades are viewed can alter the color appearance of the shades relative to the natural teeth. The color of the patient's lips and the color of gingiva contribute significantly to this background. Furthermore, the color of the natural teeth is not uniform; it typically changes in a vertical direction, from the incisal to the gingival part of the tooth and in the horizontal direction as well. The dentists try to map the color of teeth by attaching the whole dental shade to a certain part of the tooth and making a comparison. This approach is made even more difficult because the ability to choose an equivalent color is affected by the visual size of the object.

A number of devices have been proposed to assist a dentist in accurately choosing the color for dental prostheses teeth. Most of the devices aimed to replace the dentist's subjective decision by an objective measurement of color based on the illumination of teeth with polychromatic light, collecting the light that is scattered and reflected by the teeth and transforming that light into electrical signals were assumed to be adequately proportional to certain spectral components of the registered light. Determining the spectral context of light is usually performed by spectrometers that analyze continues spectra by dispersing the light with prisms or gratings or detect light at certain wavelengths by selecting it with optical filters. Measured colorimetric or spectral data from the teeth are compared with those taken from shades and stored in the memory of the device. Therefore, the closest matched shade is supposed to be chosen automatically. The photometric calorimeters that were proposed for dental application are complicated and costly to manufacture as they comprise complex integrating spheres (U.S. Pat. No. 4,881,811 to O'Brien). Simplified dental colorimeters that do not collect all scattered light, like those based on fiberoptic sensors (U.S. Pat. No. U.S. Pat. No. 4,836,674 to Lequime et al., U.S. Pat. No. 5,690,486 to Zigelbaum) or contact photoelectric calorimeters (U.S. Pat. No. 5,428,450 to Vieillefose et al) are taking light scattered by tooth differently than what appears by visual observation of natural teeth. Because of a limited aperture, the light is collected from the deeper layers of the teeth, and thus, measured spectra are affected by the thickness of the teeth and the material of the shades. Visually looking the same, teeth with differing thicknesses of enamel and different colorations of dentin will be treated by an objective photometric colorimeter as different in color. Fiberoptic proximity colorimeters are able to take signals from larger areas (U.S. Pat. Nos. 5,745,229, and 5,759,030, and 5,880,826 to Jung et al.). However, they have complex probes of multilayer fiberoptics, and, in addition, they require precise manual movement of the probe toward and away the teeth that is not convenient in the dental clinic.

An imaging device that comprises an intraoral camera, monitor, and programmable color processing means (U.S. Pat. No. 5,961,324 to Lehmann) is complicated in operation, costly, and requires extra space because of its size.

Other devices attempt to help dentist in observing the teeth and shades while giving the final decision in making the best color match to the dentist. U.S. Pat. No. 3,436,157 to Adler discloses a prismatic comparator device using a polychromatic light source which enables natural teeth to be simultaneously viewed with shades. The device, however, is bulky, comprised of four long tubes (the ends of two must be inserted in the patient's mouth to observe the patient's natural teeth). Another dental comparator device (U.S. Pat. No. 5,967,775 to Shahid) comprises a housing with a magnifying lens, a polychromatic light source and a holder of dental shades. The holder provides positioning of the shade close to the tooth, and both the tooth and shade can be viewed through the lens. This device, however, does not provide the same illumination conditions for tooth and shade as a shadow on the tooth may be created by the shade, particularly when the central part of the tooth is compared with the shade. Also, it is difficult to compare color of the tooth and shade as they typically have different sizes and shapes. In addition, the device can carry a limited number of shades because there is no space between the housing and lens, and the shades have to be manually replaced until the best color match is achieved. Furthermore, holding the housing and changing the shades requires both of the dentist's hands to be involved in handling the device. This procedure is not in convenient as the dentist needs one his hands to move the patient's lips while working with the teeth. Furthermore, in Shahid's dental comparator device, the shade prevents the lens from being constantly focused on the tooth thus requiring an exact manual focusing of the device.

SUMMARY OF THE INVENTION

It is therefore an object of the invention to provide a dental comparator scope which can be used for accurate selection of color of a dental prosthesis by viewing simultaneously the same portions of the tooth and standard dental shade.

It is also an object of the invention to provide a dental comparator scope which can provide an adequate illumination of the tooth and standard dental shade.

It is further object of the invention to provide a dental comparator scope which can provide a fixed focusing of the device on tooth and dental shade.

It is another object of the invention to provide a dental comparator scope which can be operated by a dentist with one hand.

It is an additional object of the invention to provide a dental comparator scope which can carry a plurality of dental shades, preferably most common existing dental shade guides that are well-known for dentists.

DETAILED DESCRIPTION OF THE INVENTION

Figure 1:
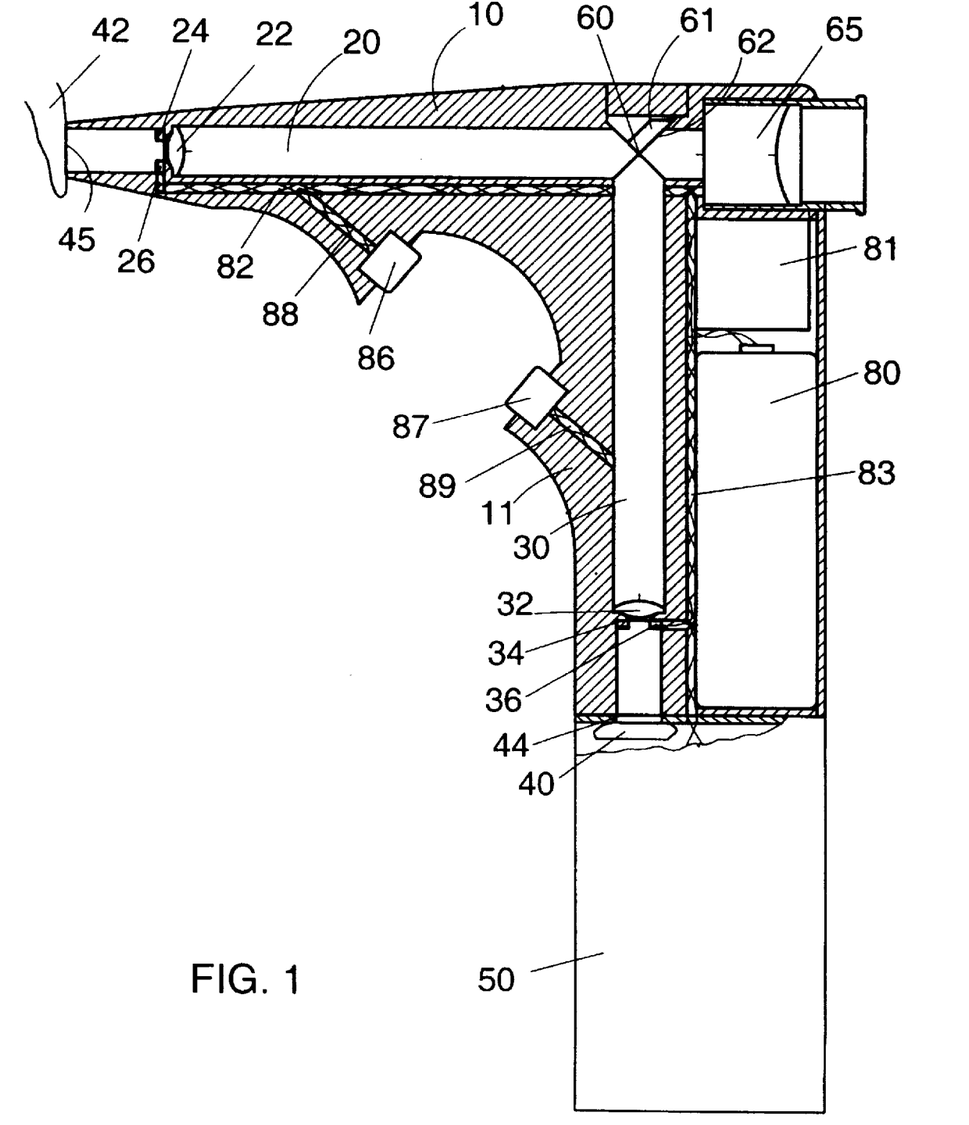
FIG. 1 is a section view of a first embodiment of the dental comparator scope of the invention including a removable cartridge which is in a stationary position with the respect to scope.

As we see from FIG. 1, the dental comparator scope generally includes an L-shape body, one part of which can be called sight (10) and another part can be called handle (11), and a cartridge (50). Two independent imaging optical channels (20) and (30) with crossing optical axes are built into the body of the dental comparator scope. The channel (20) includes a magnifying lens (22) and polychromatic light sources (24) and (26), whereas channel (30) includes a magnifying lens (32) and polychromatic light sources (34) and (36). Both lenses are identical with a focal length between 15 mm and 25 mm providing between two and five times magnification.

Figure 2:
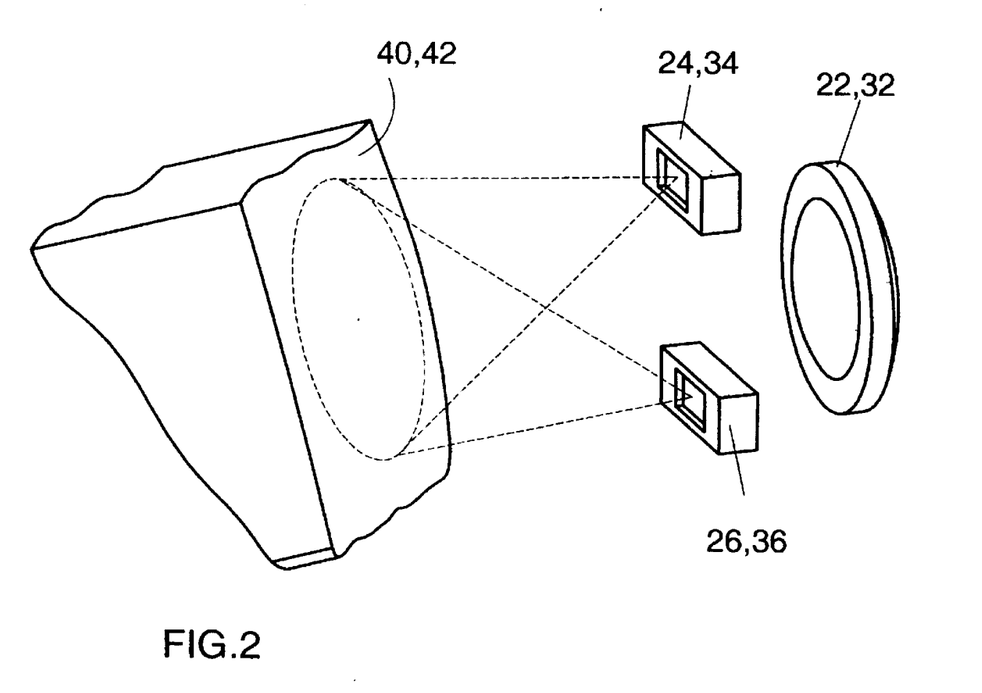
FIG. 2 is a schematic position of light sources and lens and tooth or dental shade in the dental comparator scope of FIG. 1.

The light sources (24) and (26) are located in a narrowed distal part of the sight (10) touching the tooth (42) preferably in its middle part. The light sources (34) and (36) are located in similar positions between the shade (40) and lens (32) in the bottom part of the handle (11). Light sources (24) and (26) are to provide uniform illumination of the tooth (42) with white light, and light sources (34) and (36) are to provide an adequate uniform illumination of the shade (40). The number of light sources can be different, from one in each channel to a plurality of light sources. Preferably the light sources are white light emitting diodes (LED), in particular, surface mount LEDs which provide diffuse light. They are powered from a DC power source (80), e.g., one 9 volt battery which is inserted in the body of the handle (11). The battery (80) can be connected to a voltage regulator (81) that provides an exact voltage to the LEDs, typically from 3.0 to 4.0 volts, as the energy of the battery discharges with time. The light sources are powered through wires (82) and (83) which are inserted inside of the body of the handle 11. Preferably the wires are inserted around the channels (20) and (30) thus prevent interference with the images. LEDs are identical in both channels and preferably located between the lens (22), (32) and the tooth (42) and the shade (40) as it is shown in FIG. 2.

Figure 3:
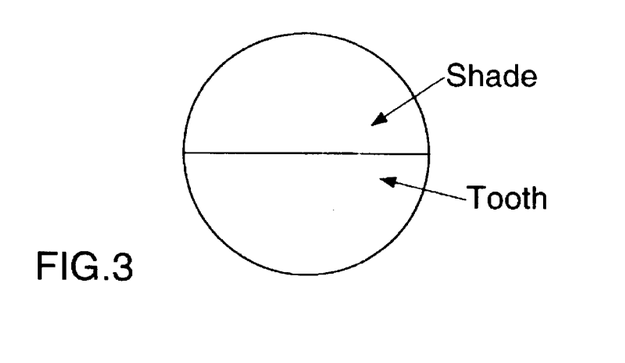
FIG. 3 is a view of the shade and tooth as it is seen in the eyepiece of the dental comparator scope by an observer.

Returning to FIG. 1, images from a portion of tooth (42) and a portion of shade (40) are formed in a plane where the optical axes of lens (22) and (32) are crossing. In this place, an edge (60) of the first surface mirror (61) is located. A reflective surface (62) of the mirror (61) faces to an eyepiece (65) that magnifies the image for the naked eye (not shown). A half of the image of shade (40) which is created by the lens (32) is forwarded to the eyepiece (65) after its reflection from the mirror surface (62). A half of the image of the tooth (42) which is formed by the lens (22) is blocked by the non-reflective surface of the mirror 61, whereas another half of the image can be viewed through the eyepiece (65). Thus two halves of the images can be seen simultaneously in the eyepiece as it is shown in FIG. 3. The upper and lower parts of the view will represent images of the shade and tooth, correspondingly. The eyepiece (65) has magnification from 5 to 20 times, preferably 15 times.

Figure 4:
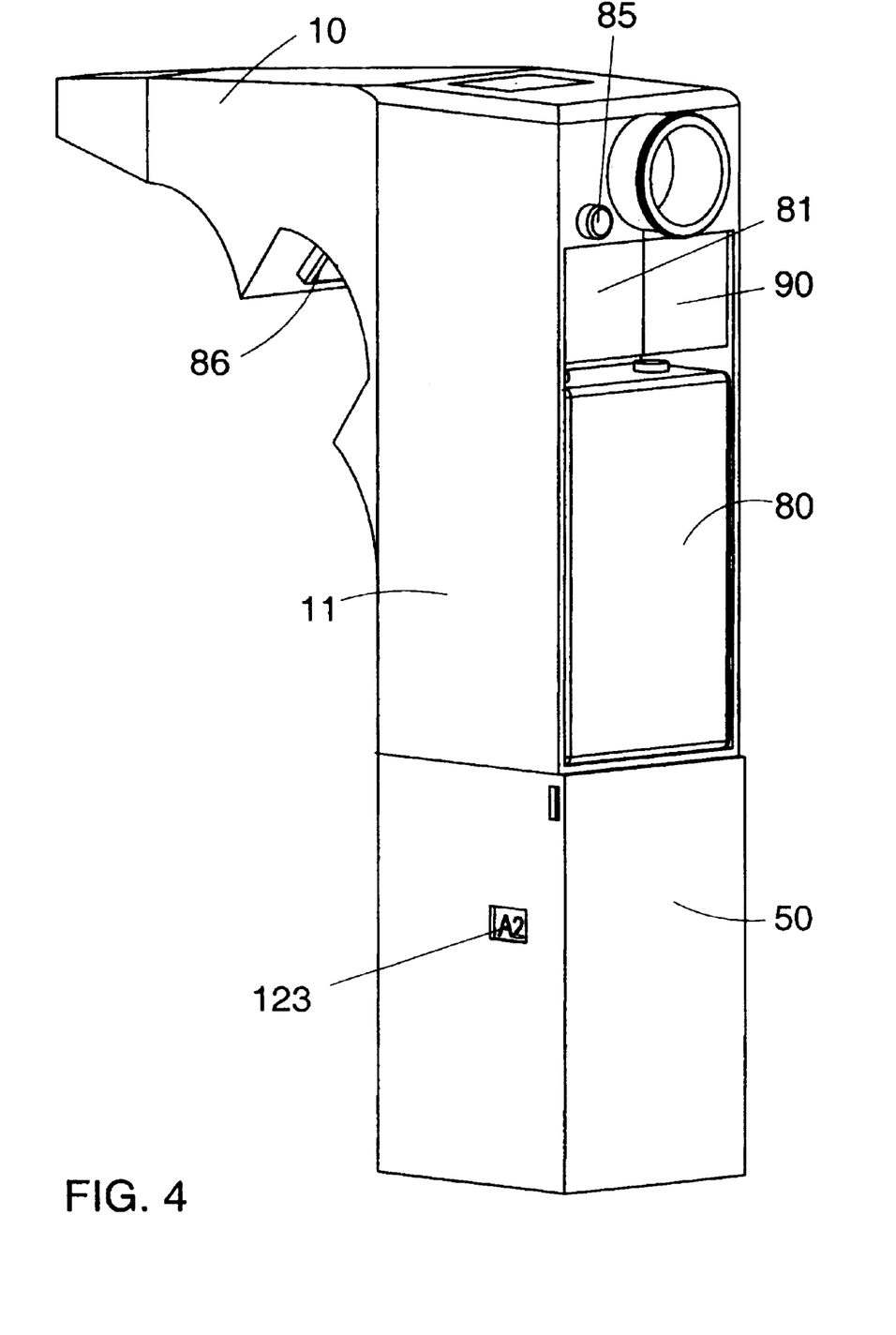
FIG. 4 is an isometric view of the dental comparator scope of FIG. 1.

In addition, the electric circuit of the dental comparator scope includes a power switch (85) that is located in a place that makes it convenient for the dentist to operate the device (preferably on the back side of the scope as shown in FIG. 4). The power switch turns on/off the battery (80). A microcontroller (90) is placed close to battery (80) and voltage regulator (81). The microcontroller can be any 8-bit microcontroller chip with few external elements required for its operation. All electronic components above are standard and allow placement on a small board using surface mount technology.

Turning to FIG. 1, two non-lock (momentary) switches (86) and (87) are located close to the corner of the L-shape body of the dental comparator scope. The distance between these switches is from 18 mm to 25 mm; thus, they can be activated with a dentist's forefinger. The switch (86) is connected to the microcontroller (90) with wires (88) which are inserted inside the body of the handle (11) in the same way as wires (82), and the switch (87) is connected to the microcontroller (90) with wires (89) which are inserted inside the body of the handle (11) and surround the channel (30) in the same way as wires (83). The switch (86) activates the movement of shade (40) inside cartridge (50) in a one direction while switch (87) activates the same movement of shade (40) in the opposite direction.

Figure 5:
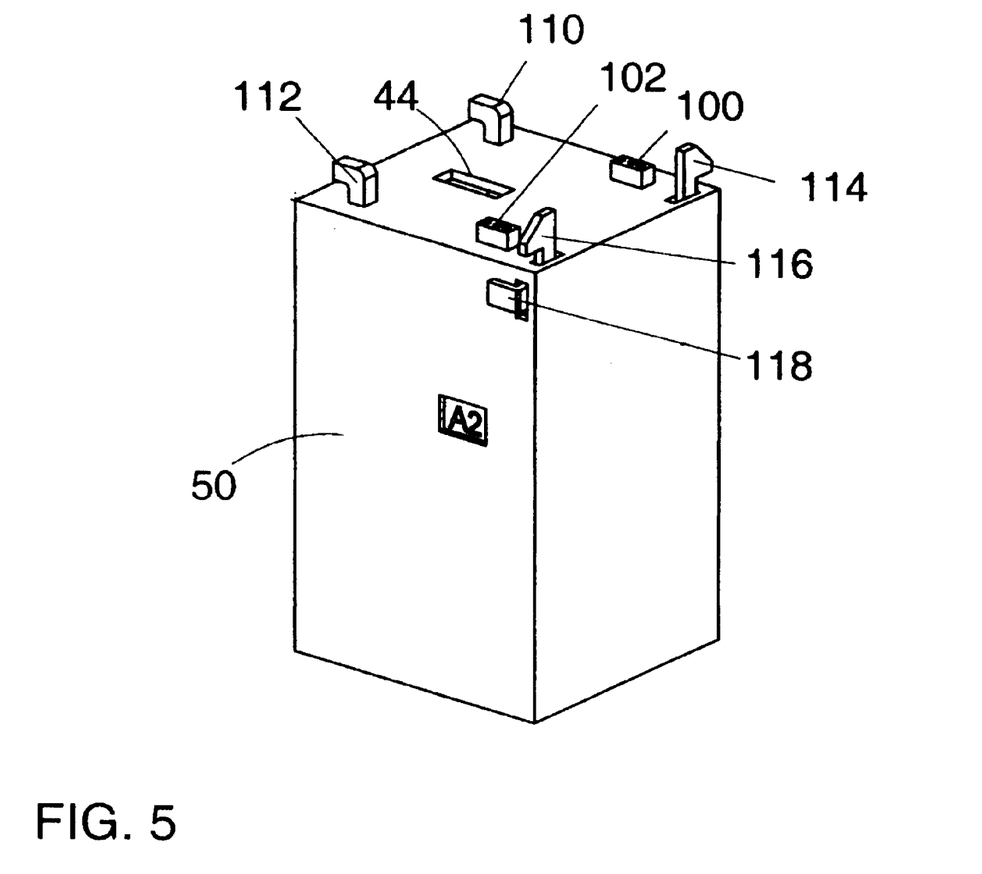
FIG. 5 is an isometric view of the cartridge detached from the dental comparator scope of FIG. 1.

The shade (40) is viewed through the aperture (44) in the removable cartridge (50); this aperture is identical to the aperture (45) that is in touch with the tooth (42). The removable cartridge (50) is attached to the bottom part of the handle (11) preferably by means of claws (110), (112) and spring-loaded catches (114), (116) as it is shown in FIG. 5. The claws and catches in the cartridge (50) have corresponding mating features in the bottom part of the scope (not shown). The cartridge (50) can be disconnected from the scope by pressing the buttons (118) (only left button is shown) and turning the cartridge until the claws are released. Connectors (100), (102) on the top of the cartridge (50) provide electrical connection to the cartridge. The connectors have mating contacts (not shown) at the bottom part of the handle (11) which are connected to the wires (83). The catches (114) and (116) can be released by pressing the buttons (118) (only the left button is shown)

Figure 6:
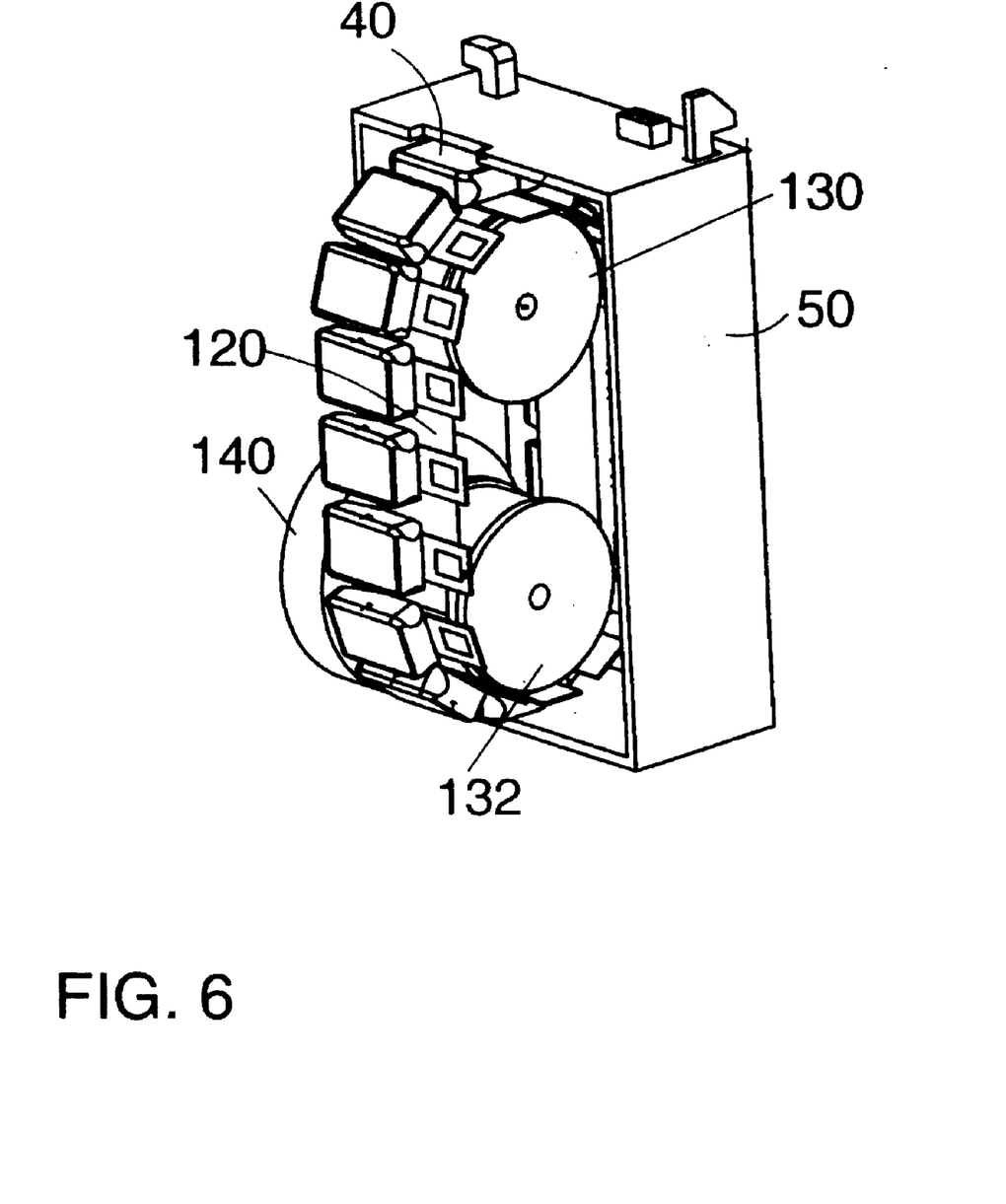
FIG. 6 is a partial section view of the cartridge of FIG. 5.

FIG. 6 discloses the content of the cartridge (50). A belt (120) with a plurality of shades on its outer surface rounds pulleys (130) and (132). The pulley (132) is mechanically connected with a motor (140). The motor (140) can be a DC micromotor with a typical voltage from two volts to five volts or a small stepper motor with a driving voltage of five volts. The motor is powered from battery (80) through microcontroller (90). Tiny micromotors like those that are used in cameras can be powered directly from the microcontroller output. Preferably the belt preferably is a timing belt with pitches from one to three millimeters, preferably two millimeters. The length of the belt depends on the number of shades carried by it and the width of the shade. For example, a full set of the Classic VITA shades guide includes 16 shades which are about 12 mm long and 8 mm wide. Therefore, the minimum length of the belt must be 128 mm.

Figure 7A:
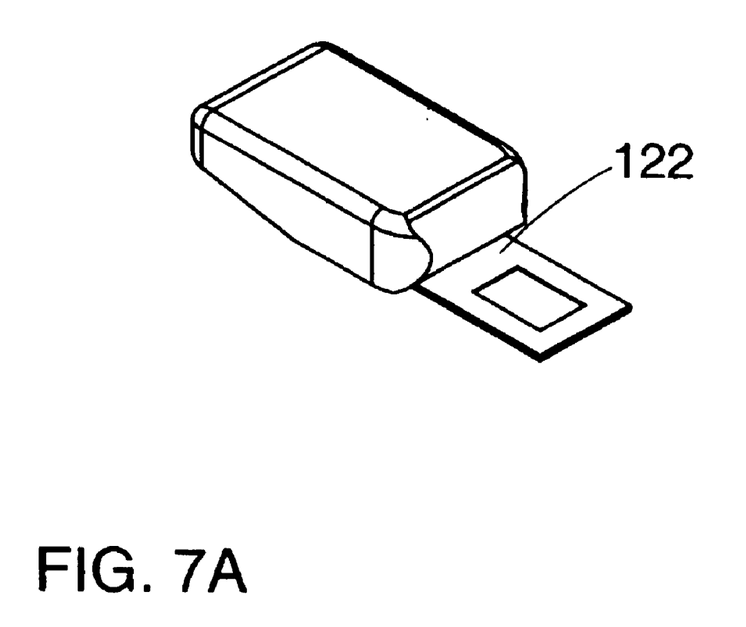
FIG. 7A is a view of a dental shade and attached holder
Figure 7B:
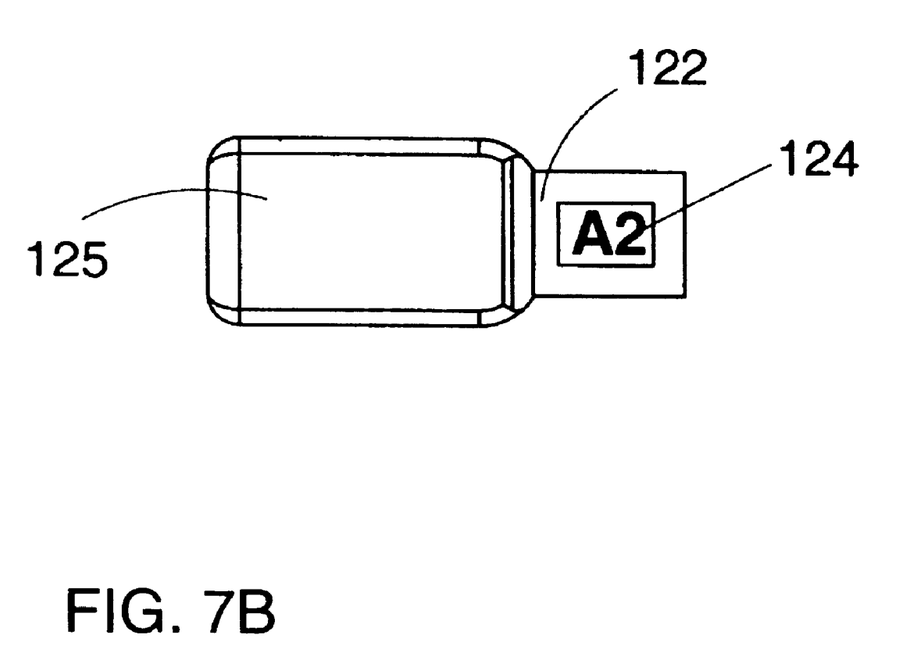
FIG. 7B is a top view of the dental shade of FIG. 7A and the holder with an identification number.

A thin short metallic holder (122) can be attached to the bottom of each shade as is shown in FIG. 7A. An identification number (124) can be written on the holder as it demonstrated in FIG. 7B. This number typically can be a conventional identification number from existing dental shade guides, like A1, A2, A3, A35, A4, B2, etc. for Classic VITA shades guide; or 1M1, 1M2, 2L1, 2L2, etc. for Vitapan 3D-Master shades guide; or B51, B53, B54, etc. for Bioform shades guide. The identification number can be viewed through the window (123) on the side of the cartridge (50) as is shown in FIG. 4. The shades on the belt (120) can be arranged in a regular order as in conventional dental shade guides or they can be arranged in a specific order, according to their value, or hue, or saturation in the Munsel color system or according to their lightness L, or value of parameters, a or b, in the Lab color system. More important is that the identification of the shades is shifted (e.g., the number A2 on the holder (122) of the shade (125) in FIG. 7B corresponds to the shade A2 that is located a few shades left or right on the belt from shade (125)). This shift provides a correct reading from the dental comparator scope indicating the shade (40) (FIG. 6) which is under aperture (44) (FIG. 1) and which is being viewed in the eyepiece.

In operation, the dentist takes the dental comparator scope, powers it by pressing the button (85), touches the distal end of the sight (10) to the patient's tooth (42), and observes images from portions of the tooth (42) and shade (40). If the tooth and the shade are significantly different in color or/and brightness, the dentist presses with the forefinger one of the buttons (86) or (87) thus activating the microcontroller (90). The microcontroller activates the motor (140) which turns the pulley (132) and moves the belt (120) until the next shade appears in the field of view. The button (86) provides forward movement of the belt whereas the button (87) provides backward movement of the belt, or vice versa. The dentist reads the number of the best matched shade from the window (123) on the side of the cartridge (50).

Figure 8:
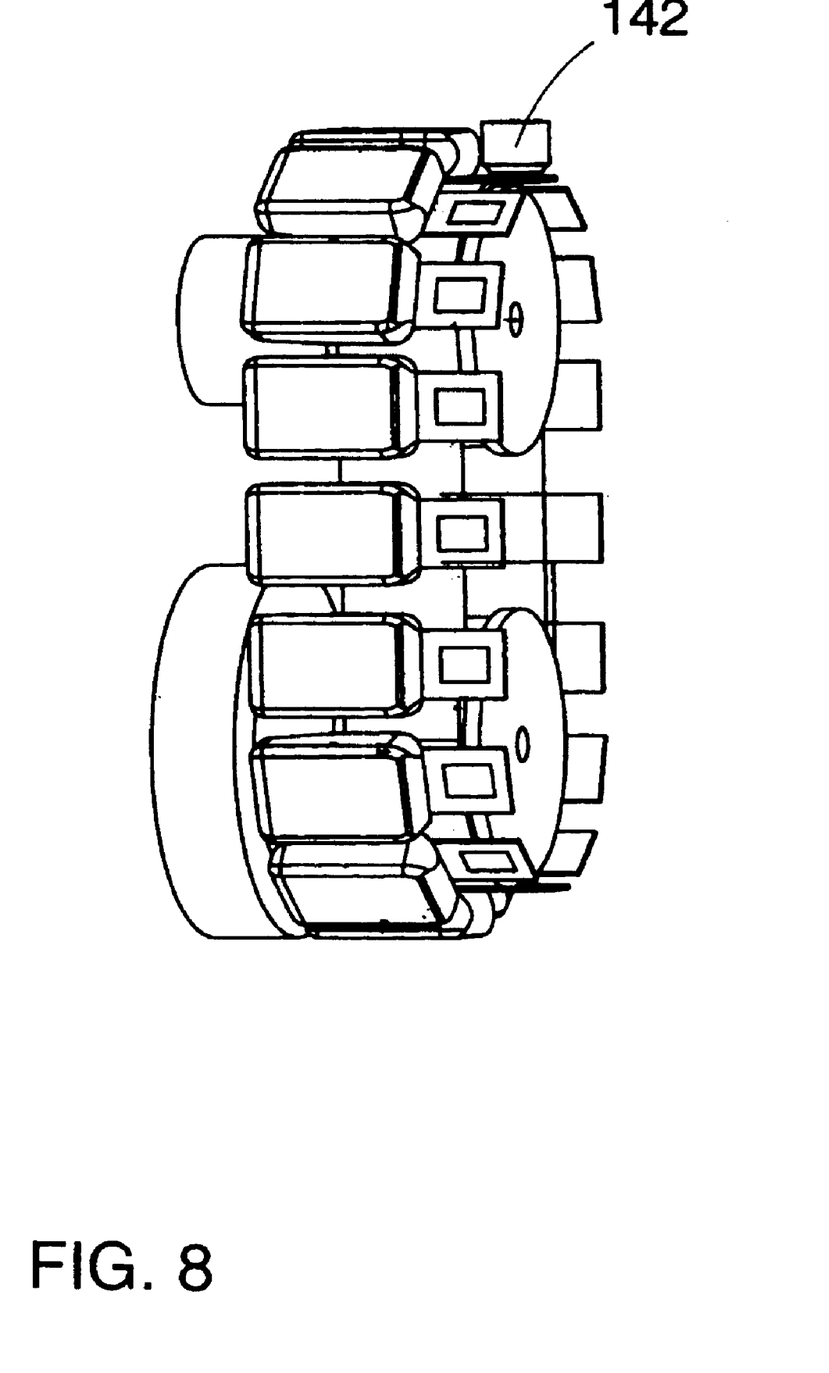
FIG. 8 is a view of the contents of the cartridge of FIG. 5.

The exact positioning of the shades against the center of the aperture (44) can be achieved by inserting a proximity sensor (142) into the cartridge (50) close to the viewing shade (40) as it is shown in FIG. 8. The sensor is a standard chip with a light source and detector powered from the battery (80) and connected to the microcontroller (90). By sensing the holder of the shade (40), the sensor delivers electrical pulses to the microcontroller (90) when the desired position of the holder is achieved, and the microcontroller stops the motor (140). The motor can be activated by periodically pressing one of the buttons (86) or (87), or by constantly pressing and holding one of them down. In this case, the microcontroller (90) activates the motor (140) in a stepper mode, namely, moving, pause, moving, pause, and so on. The duration of the pause is from a half second to five seconds, preferably one second. This pause is considered to be sufficient for the fast observation and comparison of the color of the tooth and shade.

Figure 9:
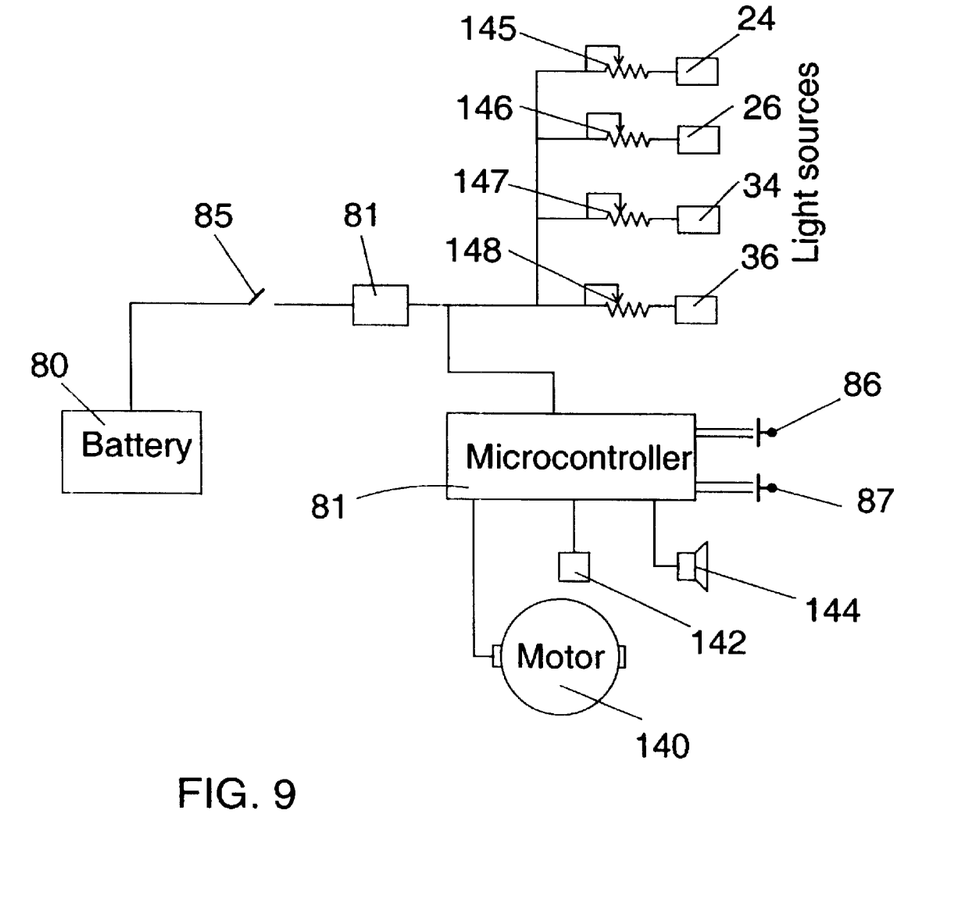
FIG. 9 is a schematic view of the electric system of the dental comparator scope.

FIG. 9 shows a schematic of the electronic circuit of the dental comparator scope. In addition to components mentioned above, a speaker (144) can be connected to the microcontroller (81). It activates by the microcontroller when new shade has been positioned against the aperture (44). Otherwise, variable resistors (145), (146), (147), (148) can be connected between the voltage regulator (81) and LEDs (24), (26), (34), and (36). The current through the LED is changed with the variation of the corresponding resistance consequently varying the brightness of the LED. This procedure may be necessary while calibrating the dental comparator scope by balancing the illumination of both fields of view, one from the tooth and another from the shade.

Figure 10:
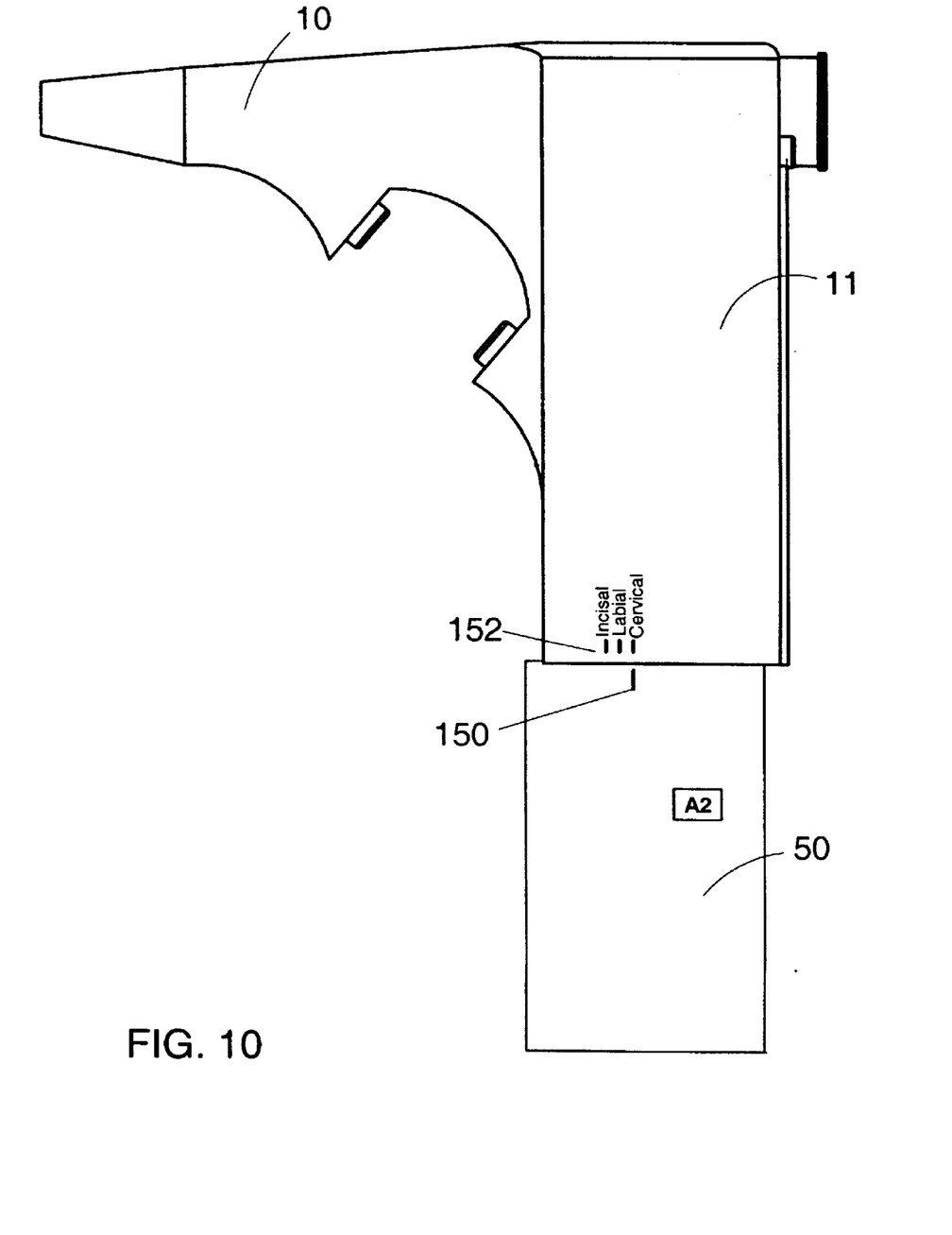
FIG. 10 is a side view of the second embodiment of the dental comparator scope with sliding cartridge.
Figure 11:
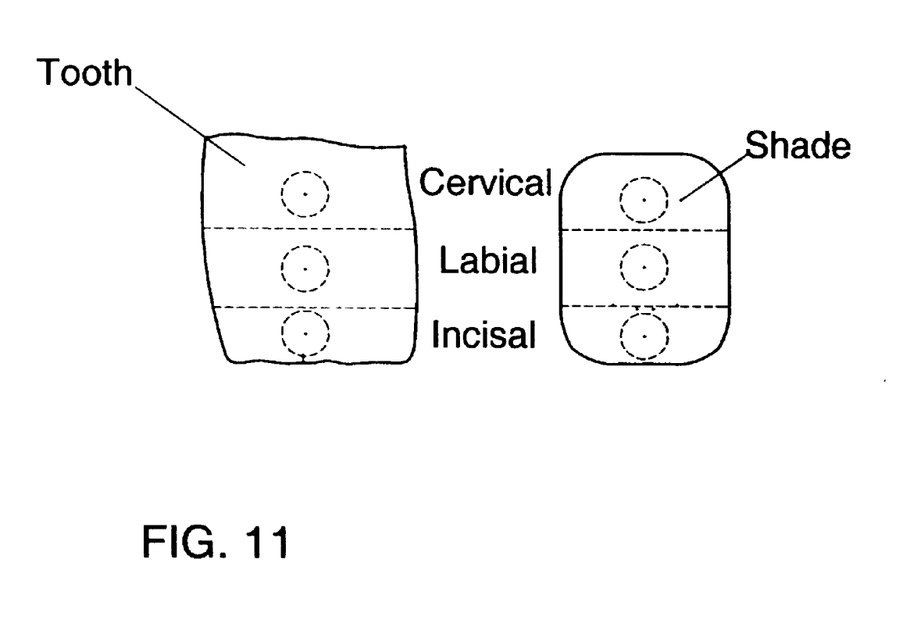
FIG. 11 is a schematic view of three zones on tooth and dental shade that can be observed with the dental comparator scope of FIG. 10.

In another embodiment of the dental comparator scope that accords with the present invention, the removable cartridge (50) can be shifted a few fixed positions along the bottom part of the handle (11) as shown in FIG. 10. A mark (150) on the cartridge (50) and marks (152) on the handle (11) indicate the position of the cartridge. A number of the marks (152) can be from two to five, preferably three, with certain indications like "Incisal", "Labial", and "Cervical", or symbols like "+", "0", and "−", or they can be marked with different colors. The shifting of the cartridge allows for the dentist to observe different zones of the shade and compare them with those from the tooth as it is shown in FIG. 11. This provides the opportunity for perfect color matching of the tooth which is typically multicolored, and the dental prosthesis. In operation, while working with the incisal part of the tooth, the dentist touches the narrow tip of the sight 10 to the incisal part of the patient's tooth. The same procedure is performed for the central (labial) and upper (cervical) zones of the tooth.

Figure 12:
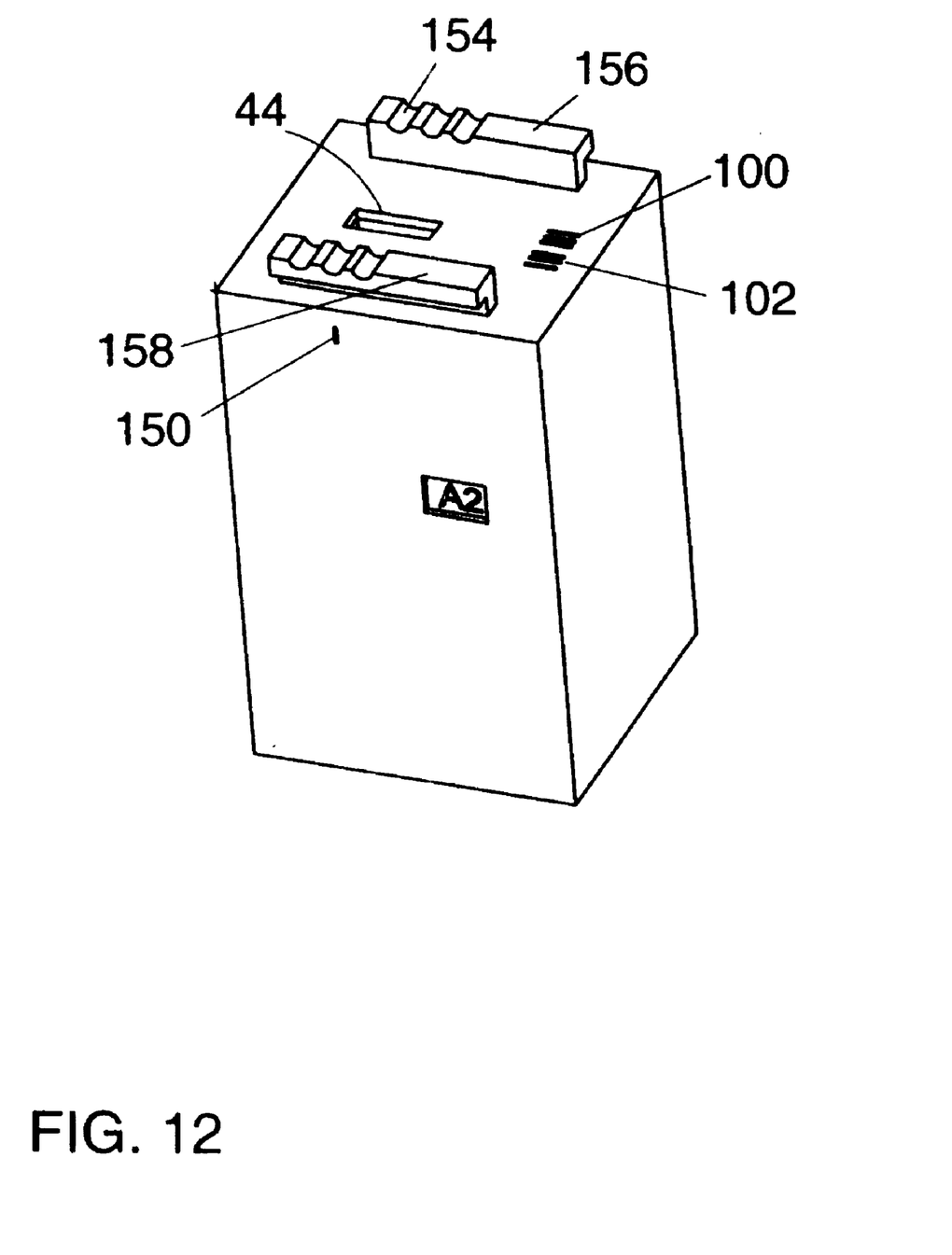
FIG. 12 is a view of the sliding cartridge of the dental comparator scope of FIG. 10.

The shifting of the cartridge can be done by a variety of means, FIG. 12 describes one of such means. Slides (154) and (156) provide positioning of the cartridge at the bottom part of the handle (11) and sliding along the direction of the sight (10) while mating with slides in the handle (11) (not shown in FIG. 10). Grooves (154) fix the cartridge at a certain position while being spring-loaded from the bottom part of the handle (11). Connectors (100) and (102) are flat sliding contacts which have mating parts at the bottom part of the handle (11) (not shown in FIG. 10).

Figure 13:
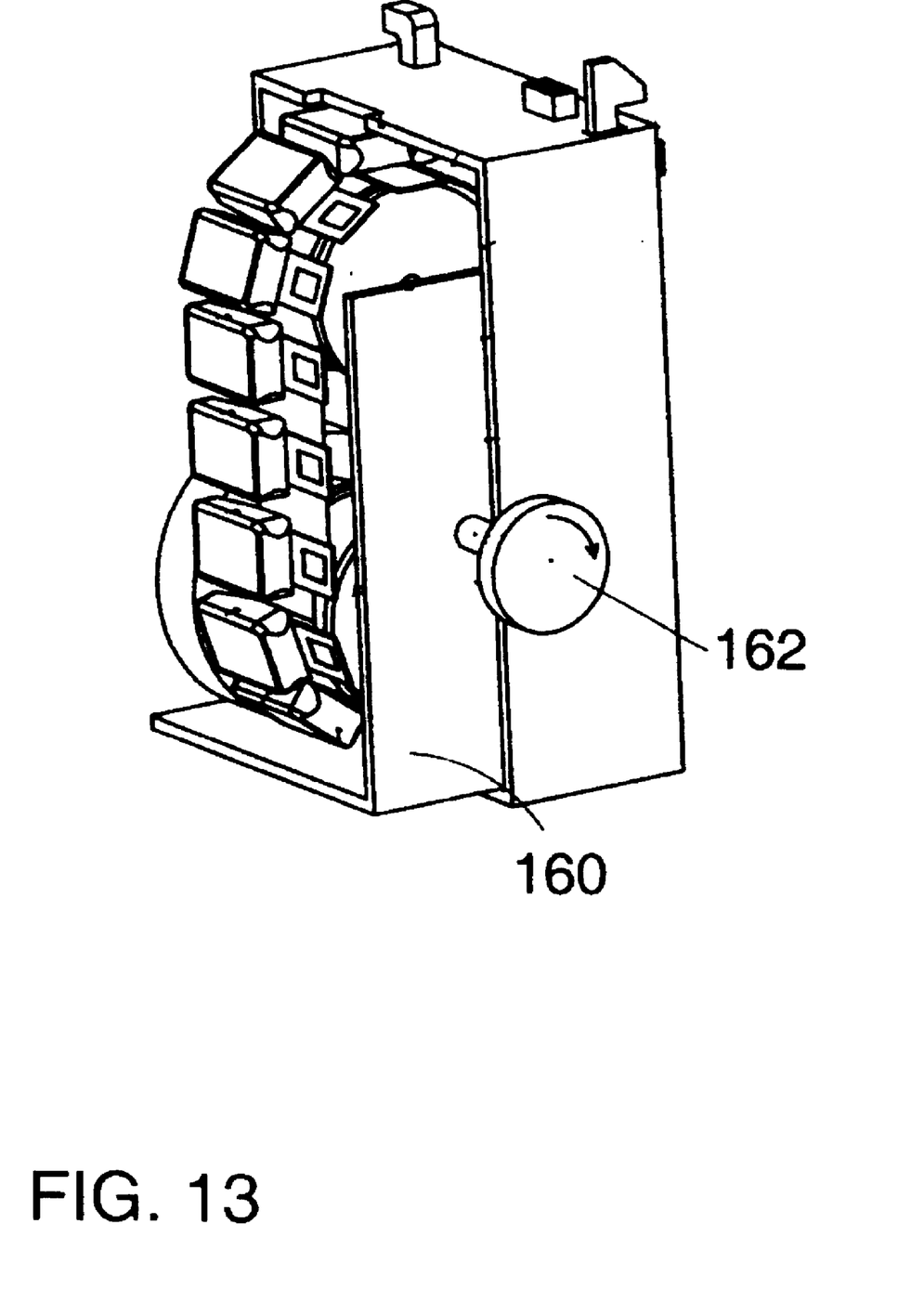
FIG. 13 is a view of the second embodiment of the cartridge with a sliding platform.

Turning to FIG. 13, the motor and pulley are assembled at movable platform (160) which can slide inside of the cartridge (50). By this means, shades can be shifted at the same positions related to aperture (44) and thus different zones of the shade can be observed. The sliding of the platform (160) can be done by different means, preferably by turning a screw (162) that is mount in the wall of the cartridge. The screw (162) can carry marks indicating which zones of the shades is being observed at the moment. The cartridge with movable platform can be connected to the bottom part of the handle (11) in the same way as that shown in FIG. 5.

Figure 14:
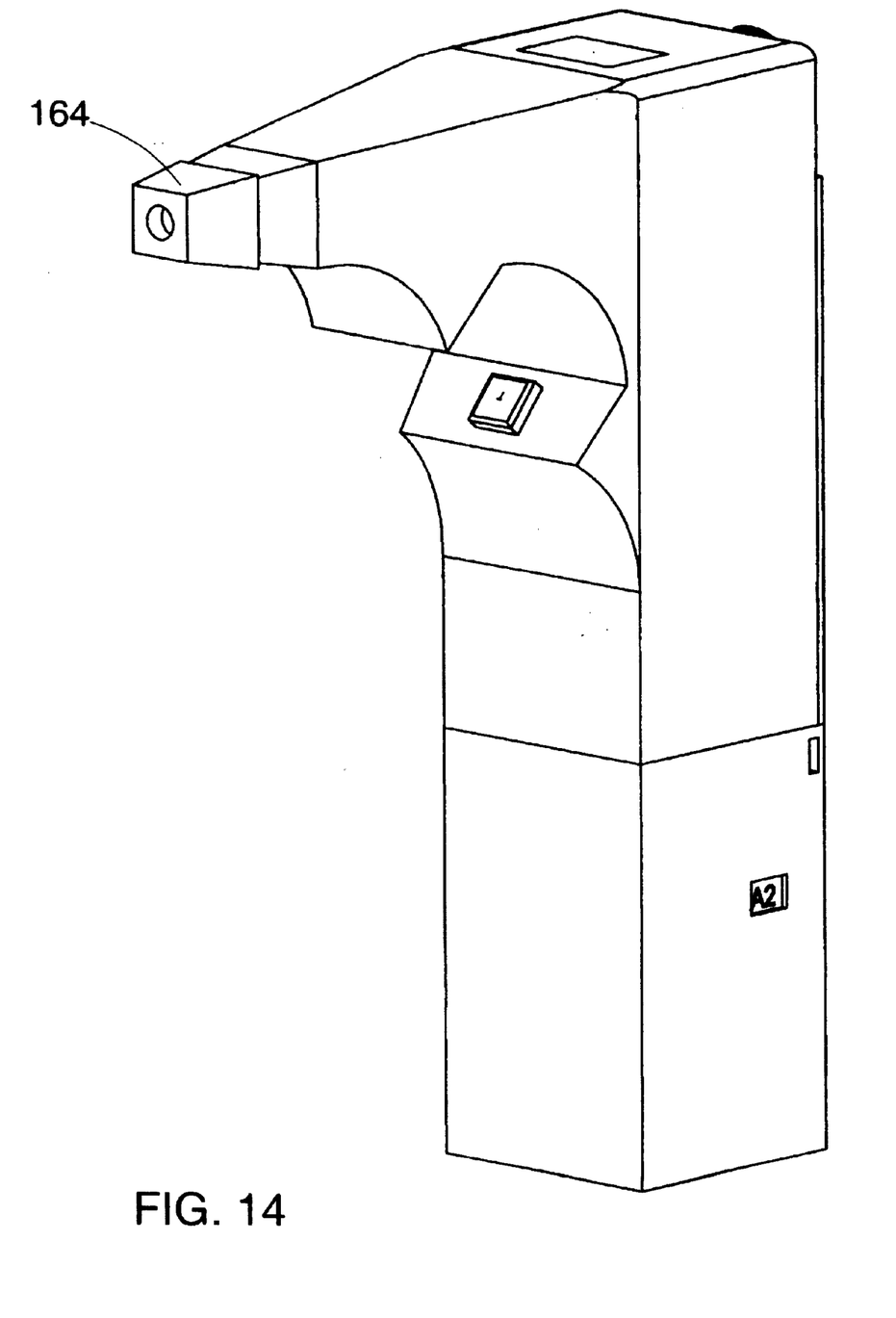
FIG. 14 is a view of the dental comparator scope of FIG. 1 with a disposable protective shield.

Finally, a disposable protective shield (164) can be applied to the distal end of the sight (10) as it is shown if FIG. 14. This shield will protect the patient against a direct contact with the scope. The shield can be made of transparent material, or it can have an aperture in the center thus not causing any distortion to illuminating and reflecting light.

There have been described and illustrated herein several embodiments of a dental comparator scope. While particular embodiments of the invention have been described, it is not intended that the invention be limited thereto, as it is intended that the invention be as broad scope as the art will allow and that the specification be read likewise. Thus, while a particular polychromatic light source has been disclosed (i.e., a white light LED) it will be appreciated that other polychromatic light sources may be used as well. Furthermore, appropriate broad-pass filters may be added to light sources to correct their colors. Also, the number of light sources can be different than that described and illustrated above. It is beneficial, but not critical, for this invention to use a symmetrical location of the light sources around the magnifying lens. The light sources can be assembled as a ring around the optical axis if they are sufficiently small (e.g. semiconductor dies or LED chips). In addition, while a certain holding has been disclosed to hold the removable cartridge to the handle, a variety of similar holdings can substitute for it. Also, different sliding holdings can be considered for shifting the cartridge and fixing its position on the handle.

What is claimed is:

1. A dental comparator scope for comparing a dental shade to a natural tooth, said dental comparator scope comprising:
    a) an L-shape body with a sight applying to said tooth and a handle;
    b) two identical optical channels with crossing optical axes, the first optical channel built in the sight, and the second optical channel build in the handle, wherein:
        said optical channels comprise light emitting means and magnifying means;
    c) a mirror which flat edge is located in the point of intersection of said both optical axes and which is tilted at 45 degrees to optical axis of said second optical channel
    d) a second magnifying means, that is coaxial to the optical axis of the first optical channel and is focused at said flat edge of said mirror.

2. A dental comparator scope according to claim 1, further comprising:
    e) a removable cartridge with dental shades which is attached to a bottom part of said handle.

3. A dental comparator scope according to claim 1, further comprising:
    f) a DC power source for providing power to illuminate said light emitting means and moving said dental shades inside said cartridge;
    g) a microcontroller for controlling the movement of said dental shades inside said cartridge.

4. A dental comparator scope according to claim 1, wherein:
    said magnifying means in each said optical channel has a power in the range of two to five times power.

5. A dental comparator scope according to claim 1, wherein
    said second magnifying means is an eyepiece of power in the range of five to twenty times power.

6. A dental comparator scope according to claim 1, wherein
    said light emitting means is located between the object and magnifying means, wherein:
        object is a tooth in the first optical channel; object is a dental shade which is in a center of said second optical channel.

7. A dental comparator scope according to claim 2, further comprising:
    a housing;
    a coupling means holding said housing with said handle;
    a connecting means providing electrical connection between said cartridge and said handle;
    a carrier with plurality of dental shades on it;
    a driving means mounted in the housing and driving the said carrier.

8. A dental comparator scope according to claim 7, wherein:
    said carrier is a belt.

9. A dental comparator scope according to claim 8, wherein:
    said belt is a timing belt.

10. A dental comparator scope according to claim 7, wherein
    said dental shades are oriented along said sight;
    said dental shades are mount equadistally on said carrier.

11. A dental comparator scope according to claim 7, wherein:
    said driving means are motor and pulleys;
    said driving means is connected to said microcontroller with said connection means.

12. A dental comparator scope according to claim 11, wherein:
    said motor is a DC micromotor.

13. A dental comparator scope according to claim 11, wherein:
    said motor is a stepper motor.

14. A dental comparator scope according to claim 7, further comprising:
    a holder that is attached to each said dental shade;
    a window in the wall of said housing.

15. A dental comparator scope according to claim 14, wherein:
    said holder can be observed from outside through said window;
    said holder has an identification number which can be read through said window.

16. A dental comparator scope according to claim 15, wherein:
    said identification number identifies a dental shade which is in the center of vision of said, second optical channel.

17. A dental comparator scope according to claim 7, wherein:
    said coupling means is a snapping means holding said cartridge in a stationary position with said handle.

18. A dental comparator scope according to claim 7, wherein:
    said coupling means is a sliding means which allows hifting said cartridge parallel to the optical axis of said first optical channel in at least two fixed positions.

19. A dental comparator scope according to claim 18, further comprising:

marks on said housing and said handle indicating positions of said shifted cartridge related to said handle.

20. A dental comparator scope according to claim 7, further comprising:

a positioning means providing an exact positioning of the dental shade in the center of view of said second optical channel.

21. A dental comparator scope according to claim 20, wherein:

said positioning means is a proximity sensor which senses a position of the holder which is close to said center of view of said second optical channel;

said positioning means is connected to said microcontroller with said connections means.

22. A dental comparator scope according to claim 7, further comprising:

a sliding platform providing a shift of said driving means and said carrier inside of said housing in at least two fixed position parallel to the optical axis of said first optical channel.

23. A dental comparator scope according to claim 7, further comprising:

a speaker which is connected to said microcontroller and signaling when the next dental shade is coming to said center of view of said second optical channel.

24. A dental comparator scope according to claim 1, further comprising:

a disposable shield with a transparent window in the center applying to a distal end of said sight and preventing direct contact of said sight with said tooth.

* * * * *